US00PP32706P3

(12) United States Plant Patent
Trigiano et al.

(10) Patent No.: US PP32,706 P3
(45) Date of Patent: Dec. 29, 2020

(54) ***CORNUS KOUSA* TREE NAMED 'MELISSA'S MOUNTAIN SNOWFALL'**

(50) Latin Name: *Cornus kousa*
Varietal Denomination: Melissa's Mountain Snowfall

(71) Applicant: UNIVERSITY OF TENNESSEE RESEARCH FOUNDATION, Knoxville, TN (US)

(72) Inventors: Robert N. Trigiano, Knoxville, TN (US); Sarah Lynn Boggess, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 16/602,154

(22) Filed: Aug. 15, 2019

(65) Prior Publication Data

US 2020/0323118 P1 Oct. 8, 2020

Related U.S. Application Data

(60) Provisional application No. 62/830,688, filed on Apr. 8, 2019.

(51) Int. Cl.
*A01H 5/02* (2018.01)
*A01H 6/00* (2018.01)
*A01H 5/04* (2018.01)

(52) U.S. Cl.
USPC ..... Plt./220
CPC ..... *A01H 5/02* (2013.01); *A01H 5/04* (2013.01); *A01H 6/00* (2018.05)

(58) Field of Classification Search
USPC ..... Plt./220
CPC ... A01H 5/02; A01H 5/00; A01H 5/04; A01H 6/00
See application file for complete search history.

(56) References Cited

PUBLICATIONS

Wadl, P. A. et al. "Three New Cultivars of *Cornus kousa*: Empire, Pam's Mountain Bouquet, and Red Steeple" *HortScience*, Sep. 2014, pp. 1230-1233, vol. 49, No. 9.

*Primary Examiner* — June Hwu
(74) *Attorney, Agent, or Firm* — Saliwanchik, Lloyd & Eisenschenk

(57) ABSTRACT

A new and distinct cultivar of flowering dogwood tree, which has fused bracts is provided. This dogwood tree is botanically known as *Cornus kousa* and referred to by the following cultivar name: 'Melissa's Mountain Snowfall'.

3 Drawing Sheets

Specification includes a Sequence Listing.

This invention was made with Government support under Contract No. NACA-58-6062-6 awarded by the U.S. Department of Agriculture. The Government has certain rights in the invention.

Latin name of the genus and species: *Cornus kousa.*

Variety denomination: 'Melissa's Mountain Snowfall'.

The Sequence Listing for this application is labeled "Seq-List.txt" which was created on Nov. 1, 2019 and is 4 KB. The entire content of the sequence listing is incorporated herein by reference in its entirety.

BACKGROUND OF THE INVENTION

The present invention relates to a new and distinct dogwood cultivar, which has fused bracts. This dogwood is botanically known as *Cornus kousa* 'Melissa's Mountain Snowfall', hereinafter referred to as 'Melissa's Mountain Snowfall'. The unique characteristic of this variety is the non-overlapping fusion of the bracts, shape of the tree, and bark characteristics.

This new dogwood cultivar was discovered in a planting of seedlings in the University of Tennessee Arboretum in Oak Ridge, Tenn. 'Melissa's Mountain Snowfall' is a half-sibling of 'Pam's Mountain Bouquet' (U.S. Plant Pat. No. 25,575; Wadl et al., 2014, HortScience 49(9):1230-1233).

Asexual reproduction of 'Melissa's Mountain Snowfall' in Belvidere, Tenn. was by axillary bud grafting onto a generic *Cornus kousa* seedling rootstock and has shown that the unique features of this new dogwood cultivar are stable and reproduced true-to-type in successive vegetative generations.

DETAILED DESCRIPTION OF THE NEW VARIETY

Figure 1:
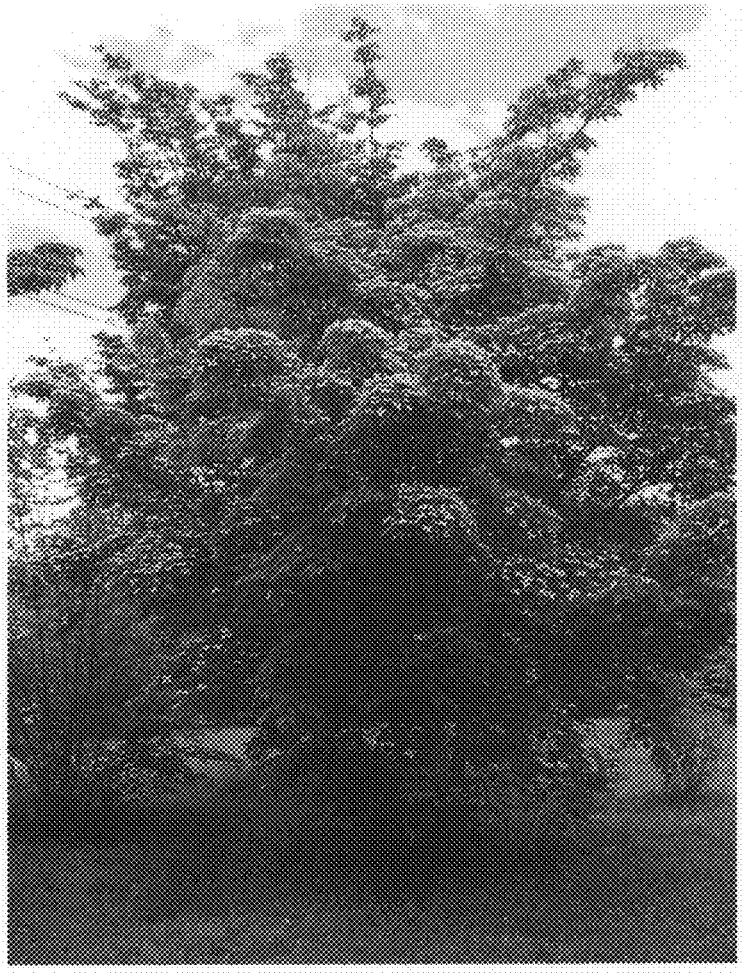
FIG. 1. Photograph of a 'Melissa's Mountain Snowfall' tree that is approximately 30 years old. The spread of this tree is about 7 meters. Colors in the photograph may differ from actual colors due to lighting and light reflectance.

A new and distinct cultivar of flowering dogwood having fused bracts is provided. This dogwood tree cultivar is botanically known as *Cornus kousa* and referred to by the cultivar name: 'Melissa's Mountain Snowfall'. This cultivar exhibits insect resistance and disease resistance, particularly to powdery mildew caused by *Erysiphe pulchra*. Dogwood anthracnose caused by *Discula destructiva* has never been observed on 'Melissa's Mountain Snowfall'.

The subject cultivar is different compared to the *Cornus kousa* varieties 'Red Steeple' and 'Empire'. The following Table 1 sets forth the difference between these cultivars and 'Melissa's Mountain Snowfall':

TABLE 1

Characteristics of 'Melissa's Mountain Snowfall' compared with two similar cultivars

| 'Melissa's Mountain Snowfall' | 'Red Steeple' | 'Empire' |
|---|---|---|
| Habit Spreading | Narrow Linear - short columnar | Narrow linear Tall Columnar |
| Fused Bracts | Non-fused bracts | Non-fused bracts |
| Large Bracts white | Small bracts - some pink margin | Small bracts |

This new and distinct dogwood tree cultivar was discovered in a planting of seedlings within the Arboretum at the University of Tennessee located in Oak Ridge, Tenn. The subject dogwood tree cultivar is a half-sibling of the *Cornus kousa* dogwood cultivar known as 'Pam's Mountain Bouquet'. Table 2 shows the observed phenotypic similarities and differences between the two cultivars.

TABLE 2

General phenotypic differences between the dogwood cultivars 'Melissa's Mountain Snowfall' and 'Pam's Mountain Bouquet'.

| 'Melissa's Mountain Snowfall' | 'Pam's Mountain Bouquet' |
|---|---|
| About 80% of all bracts on the cultivar exhibit some degree of fusion | About 82% of all bracts on the cultivar exhibit some degree of fusion |
| Resistance to Disease and Insect Damage | Resistance to Disease and Insect Damage |
| Exfoliating bark in older specimens** | No exfoliating bark |
| Inverted pyramidal growth habit** | Spreading growth habit |
| Multiple leaders** | Single leader |
| Six meters in height** | 3-4 meters in height |

(** = Key differences)

In addition to the phenotypic differences listed above, it has also been observed that the alleles of the two cultivars differ at 5 of 8 selected loci. Asexual reproduction of 'Melissa's Mountain Snowfall' by grafting of axillary buds onto generic *Cornus kousa* seedling rootstocks has shown that the unique features of this new dogwood cultivar are stable and reproduced true-to-type in successive generations.

DETAILED BOTANICAL DESCRIPTION

The following observations, measurements and comparisons describe the cultivar 'Melissa's Mountain Snowfall' grown in Oak Ridge, Tenn. Trees used for this description were about thirty (30) years old. Plant hardiness is expected to be zones 3-9. The color characteristic descriptions use color references to The Royal Horticultural Society (R.H.S.) Colour Chart, The Royal Horticultural Society, London, UK, 4$^{th}$ Edition, 2001, except where general terms of ordinary dictionary significance are used. It has been determined that alleles differ at 5 of 8 loci shared by 'Melissa's Mountain Snowfall' and 'Pam's Mountain Bouquet', as shown in Table 3.

TABLE 3

Allelic Comparison of 'Melissa's Mountain Snowfall' and 'Pam's Mountain Bouquet' at specified loci

| Locus | 'Melissa's Mountain Snowfall' (bp size for each allele) | 'Pam's Mountain Bouquet' (bp size for each allele) |
|---|---|---|
| CK005* | 228:228 | 222:247 |
| CK072* | 113:122 | 113:117 |
| CK058* | 152:152 | 148:148 |
| CK031 | 140:140 | 140:140 |
| CK040* | 102:102 | 94:94 |
| CK029 | 90:102 | 90:102 |
| CK015* | 119:122 | 130:136 |
| CK047 | 128:128 | 128:128 |

Table 4 indicates the primer sequences and microsatellite markers (or single sequence repeats—SSR) in 'Melissa's Mountain Snowfall' compared with the same microsatellite markers (SSR) in 'Pam's Mountain Bouquet.' Those loci indicated with an asterisk (*) differ between the two cultivars.

TABLE 4

Primer Sequences and Microsatellite markers compared between 'Melissa's Mountain Snowfall' and 'Pam's Mountain Bouquet'

| GenBank Accession No. | Locus | Microsatellite Repeat Sequences: Primer Sequence (5'-3') | Repeat Motif |
|---|---|---|---|
| EU544308 | CK005* | F:GCATTTGTCCTTTGTTTGACAT (SEQ ID 1) R:TTTTTCGCGAAGTGTTCTCTAC (SEQ ID 2) | $(AC)_{20}$ |
| EU125523 | CK015* | F:GTCAAATTTTTGATCTTTCTCTCT (SEQ ID 3) R:GGAGAGACAGAGTACAGTAGAGGT (SEQ ID 4) | $(CT)_{10}$ |
| EU125524 | CK029 | F:AATTTAGGTTAAGGTTTTGATTTG (SEQ ID 5) R:AGAGAGAATAGGTTACAGCATCAT (SEQ ID 6) | $(TC)_{8}$ |
| EU125525 | CK031 | F:TGTCACTGCTTACAGAAACAAT (SEQ ID 7) R:TATGACGAGATTGTATAAGTTGCT (SEQ ID 8) | $(CT)_{7}$ |
| EU125526 | CK040* | F:CCAAGTCAGTTTGGTAGTAATTC (SEQ ID 9) R:AGTGCAACTTTTACTTGCTATGT (SEQ ID 10) | $(GT)_{16}$ |
| EU544309 | CK058* | F:CTTAAGTCACAAAGACAATGAAAT (SEQ ID 11) R:AAGAGAGTTCAGATTTATCTTTGC (SEQ ID 12) | $(GT)_{10}$ |
| EU544312 | CK072* | F:AGCACTCATAGTCCTTGCAC (SEQ ID 13) R:GTTAAAACGAAGAAGATACAACAA (SEQ ID 14) | $(GT)_{10}$ |

TABLE 4-continued

Primer Sequences and Microsatellite markers compared between 'Melissa's Mountain Snowfall' and 'Pam's Mountain Bouquet'

| GenBank Accession No. | Locus | Microsatellite Repeat Sequences Primer Sequence (5'-3') | Repeat Motif |
|---|---|---|---|
| EU125528 | CK047 | F:GAAAGAGATAAAAGATGGTTCAAT (SEQ ID 15) R:CTTATAGAGTAAGCCCACCATC (SEQ ID 16) | $(AC)_6$ |

The cultivar 'Melissa's Mountain Snowfall' has some similarity in phenotypic characteristics to the cultivar 'Pam's Mountain Bouquet' (Wadl et al., 2014). The following Table 5 provides a comparison of each cultivar for those characteristics that have been observed. Measurements are provided as an average (with ranges also provided as indicated):

TABLE 5

Characteristics of 'Melissa's Mountain Snowfall' and Pam's Mountain Bouquet'
Color Descriptions are based upon the Royal Horticultural Society's (RHS) colour chart, 4th Edition 2001.

| | Character | 'Melissa's Mountain Snowfall' | 'Pam's Mountain Bouquet' |
|---|---|---|---|
| 1 | Tree form (observation) | Inverted pyramidal | spreading |
| 2 | Tree height (observation) | 5-6 meters height and about a 7 meter spread | low (about 3-4 meters; spread about 4-5 meters, and dependent on age and environment) |
| 3 | Branch thickness (measurement) Thickness in the middle portion of a plant | Medium Variable, dependent on age | medium (age dependent) |
| 4 | Color of current Shoot (observation) Current shoot color in the middle portion of a plant | Green 144A turning Greyed-Green 197A | Green 143B |
| 5 | Branch color (observation) Current branch color in the middle portion of a plant by second year | Mixture of 156A, 197B, 198B, 200C and 200D | Greyed-Green 198B |
| 6 | Dark spots on Branch (observation) Presence of dark spots on the branch | Absent | Absent |
| 7 | Branching (observation) Density of branching | High | High |
| 8 | Internode length (measurement) Internode length in the middle portion of a plant | Mostly short, but some intermediate (variable + 6-9 cm) | Short |

TABLE 5-continued

Characteristics of 'Melissa's Mountain Snowfall' and Pam's Mountain Bouquet'
Color Descriptions are based upon the Royal Horticultural Society's (RHS) colour chart, 4th Edition 2001.

Figure 2:
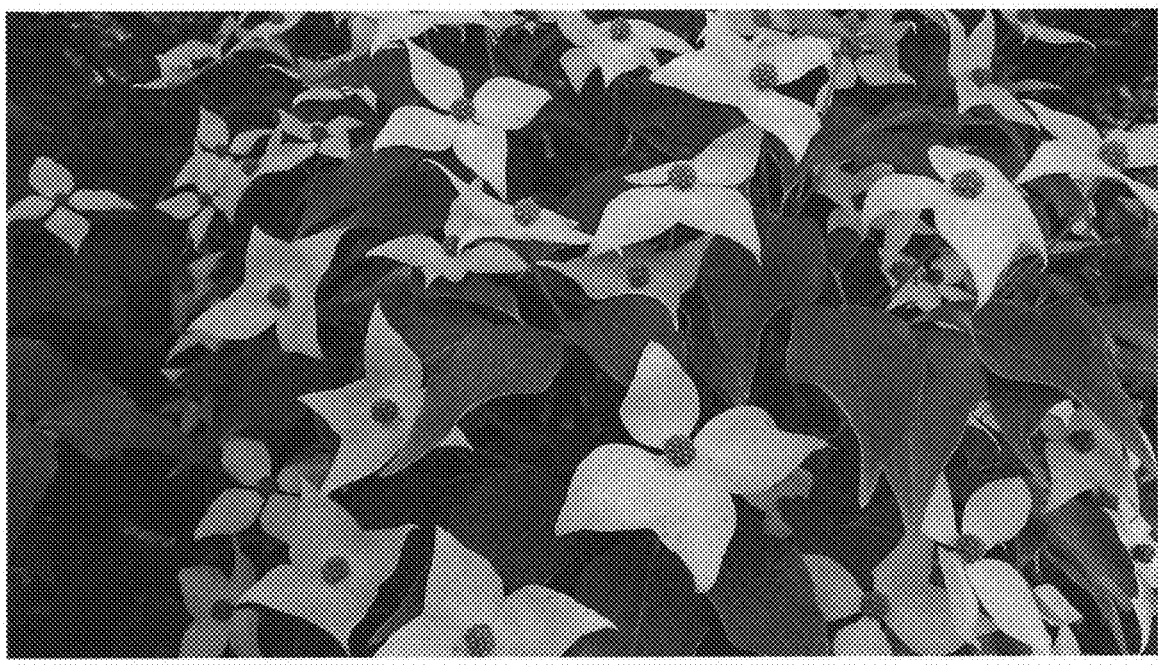
FIG. 2. Photograph of enlarged view of bracts on 'Melissa's Mountain Snowfall'.
Figure 3:
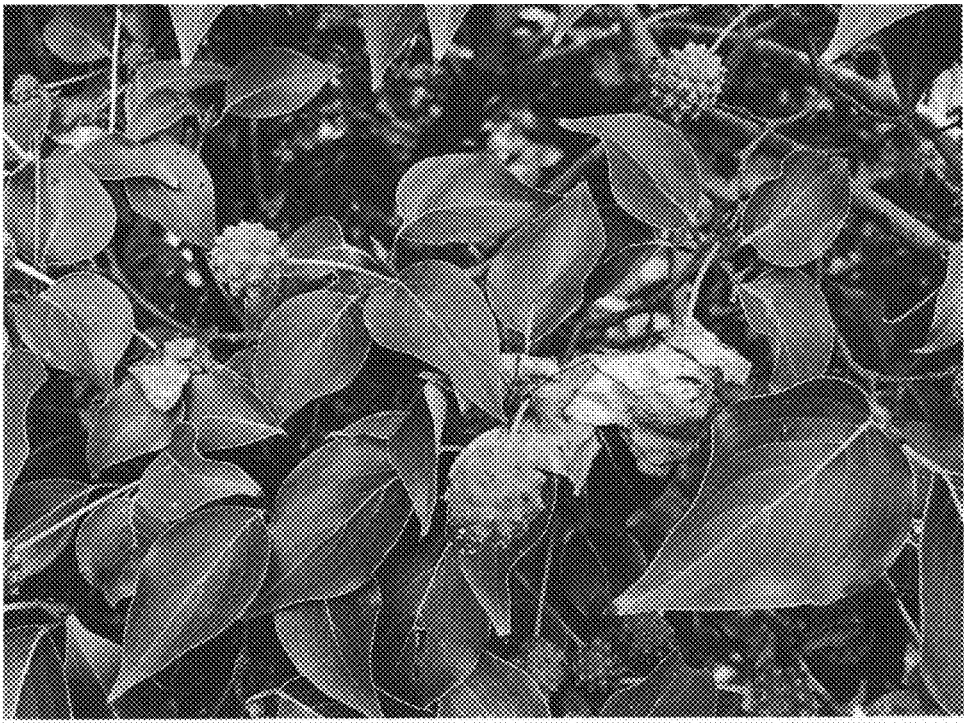
FIG. 3. Photograph of the unripe fruit of 'Melissa's Mountain Snowfall'. Also shown are the paper collars of the dried bracts that remain on the petioles and around the fruit.
Figure 4:
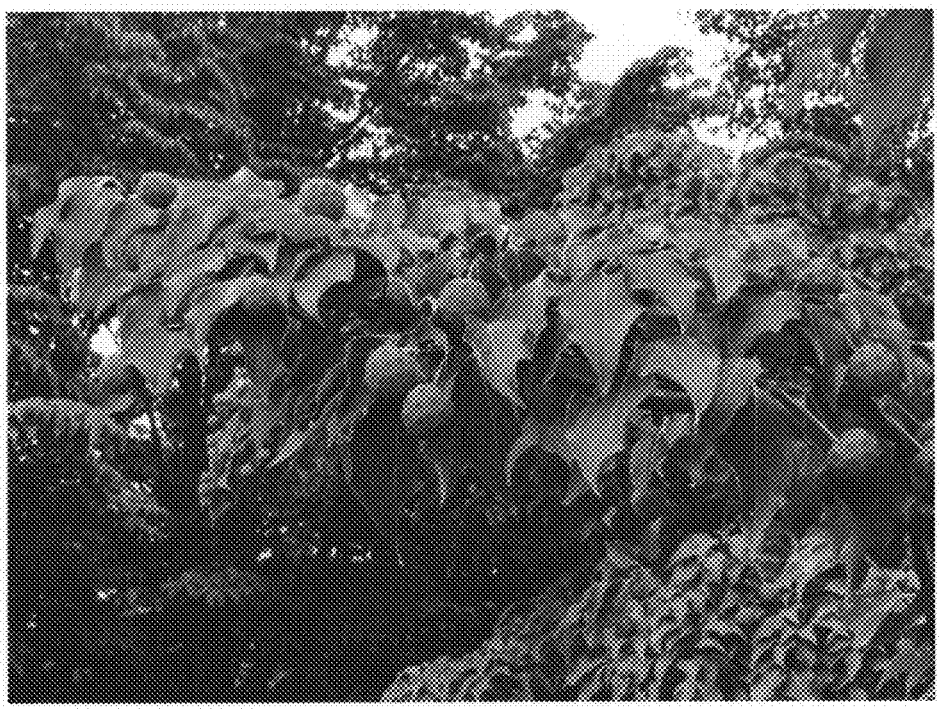
FIG. 4. Photograph of the ripe fruit of 'Melissa's Mountain Snowfall'.
Figure 5:
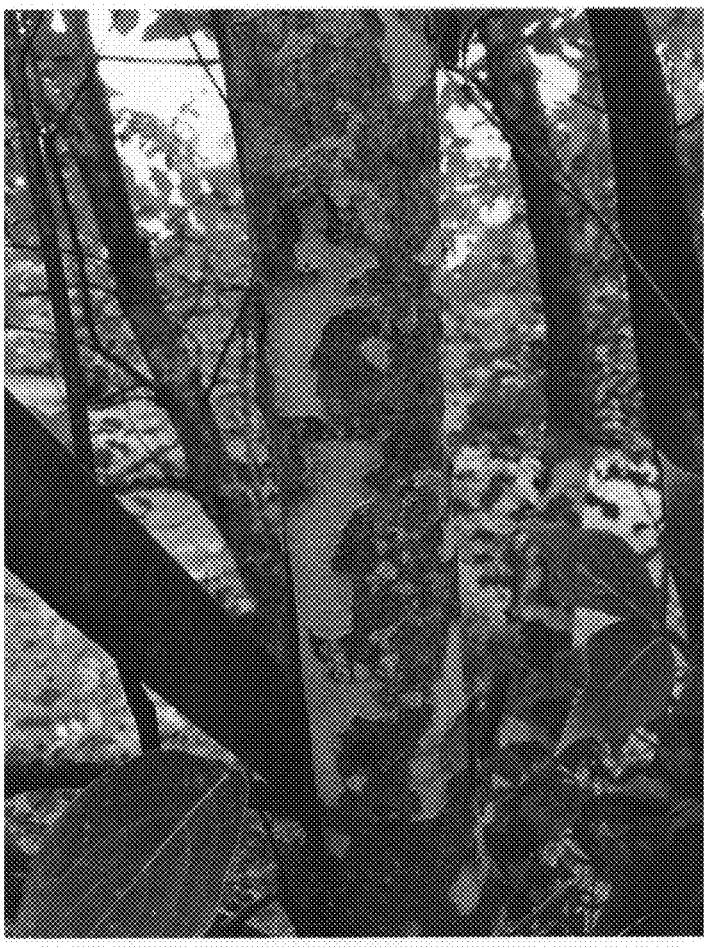
FIG. 5. Photograph showing the exfoliating bark on the trunk of older specimens of 'Melissa's Mountain Snowfall'.

| | Character | 'Melissa's Mountain Snowfall' | 'Pam's Mountain Bouquet' |
|---|---|---|---|
| 9 | Whole shape of leaves (observation) see FIGS. 2, 3 and 4 Whole shape of a leaf in the middle portion of a plant | Obovate | Obovate |
| 10 | Shape of leaf tip (observation) see FIG. 2 Tip shape of a leaf in the middle portion of a plant | Acuminate | Acuminate |
| 11 | Shape of leaf Base (observation) see FIG. 2 Base shape of a leaf in the middle portion of a plant | Truncate | Truncate |
| 12 | Shape of leaf Margin (observation) Shape of a leaf margin in the middle portion of a plant | Entire | Entire |
| 13 | Leaf rolling (observation) see Fig. 4 | Typically none, but some inward | Rolling inward |
| 14 | Leaf curvature (observation) | Mostly flat | Flat |
| 15 | Leaf margin Undulation (observation) | Some leaves undulating | None |
| 16 | Leaf length (measurement) Length from the tip to the base of mature leaf | Averages 87.1 mm | Long (about 100-400 mm) |
| 17 | Leaf width (measurement) The maximum width of mature leaf | Mean 44.4 mm | Narrow (about 40-50 mm) |
| 18 | Leaf thickness (observation) Thickness of mature leaf | Medium | Medium |
| 19 | Bud color (observation) Color of bud just after sprouting | Green 138B, unopened; Green 132D, opened; infrequently Yellow-Green 151C | Greyed-red 179A |
| 20 | Immature leaf color (observation) | Not observed | Green 135B |
| 21 | Presence of anthocyanin (observation) Coloration by anthocyanin on the immature leaf upperside | Absent | Absent |
| 22 | Color of leaf upperside (observation) Color of mature leaf upperside | Green 143A | Green 143B |
| 23 | Color of leaf Lower side (observation) Color of mature leaf lower side | Green 143B; Green 143C | Yellow-Green 146B |

TABLE 5-continued

Characteristics of 'Melissa's Mountain Snowfall' and Pam's Mountain Bouquet'
Color Descriptions are based upon the Royal Horticultural Society's (RHS) colour chart, 4th Edition 2001.

| | Character | 'Melissa's Mountain Snowfall' | 'Pam's Mountain Bouquet' |
|---|---|---|---|
| 24 | Seasonal change of a mature leaf (observation) | Changed | Changed |
| 25 | Color of leaves in autumn (observation) | Yellow to Red (Variable) Changes in Leaf Fall Color 10C-46A | Red 10C-46A |
| 26 | Leaf variegation (observation) Variegation on leaf upper side | Not variegated | Not variegated |
| 27 | Variegation pattern (observation) Pattern of variegation on a leaf upperside | NA | NA |
| 28 | Variegation color (observation) | NA | NA |
| 29 | Seasonal change of variegation color (observation) | NA | NA |
| 30 | Hair on leaf upperside (observation) Hair density on a mature leaf upperside | None | None |
| 31 | Hair on leaf lowerside (observation) Hair density on a mature leaf lowerside | None | None |
| 32 | Petiole length (measurement) Length from the base of blade to the base petiole | Short about 10.4 mm; unequal at base, about 5-7 mm longer on one side | Short (about 15-25 mm) |
| 33 | Petiole width (measurement) The maximum width of a mature leaf petiole | Medium (<7 mm) | Medium (<8 mm) |
| 34 | Petiole color (observation) | Green 143A-143C | Green 143B |
| 35 | Inflorescence type (observation) | Umbel | Umbel |
| 36 | Inflorescence direction (observation) | Upright | Upright |
| 37 | Inflorescence diameter (observation) | Average about 31.7 mm | Medium (diagonal mean length = 74 mm; mean width = 53 mm) |
| 38 | Flower diameter (measurement) | Small; Each about 5-7 mm | Small |
| 39 | Floret color (observation) | Yellow-Green 151A | Yellow-Green 150C |
| 40 | Bract type (observation) | 80% are fused, but variable (See Table 6) | 83% are fused, but variable (See Table 2) |
| 41 | Uniformity of bract size (observation) | Not uniform | Not uniform |
| 42 | Bract overlapping (observation) | No overlap of unfused bracts | No overlap of unfused bracts |
| 43 | Bract orientation (observation) | Recurved, Reflexed, or Flat | Recurved, Reflexed, or Flat |
| 44 | Bract rolling (observation) | Varies (may roll inward or outward) | Varies (may roll inward or outward) |
| 45 | Degree of bract rolling (observation) | Medium | Strong |
| 46 | Bract curvature (observation) | Varies (can be recurved, flat, or reflexed) | Varies (can be recurved, flat, or reflexed) |

TABLE 5-continued

Characteristics of 'Melissa's Mountain Snowfall' and Pam's Mountain Bouquet'
Color Descriptions are based upon the Royal Horticultural Society's (RHS) colour chart, 4th Edition 2001.

| | Character | 'Melissa's Mountain Snowfall' | 'Pam's Mountain Bouquet' |
|---|---|---|---|
| 47 | Bract twisting (observation) | None | None |
| 48 | Whole shape of bracts (observation) | Ovate | Ovate |
| 49 | Shape of bract apex (observation) | Acuminate | Acuminate |
| 50 | Unfused bract length (measurement) | Inner Bract Average 48 mm; Outer Bract Average 43 mm | Medium |
| 51 | Unfused Bract width (measurement) | Inner Bract Average 27 mm; Outer Bract Average 28 mm | |
| 52 | Number of bracts (measurement) | 4 FUSED; Diameter average 89.5 mm, all four bracts fused, after flowering remains as a papery collar (Grey-Brown 199D) at base of the petiole | FUSED, but 4 |
| 53 | Bract color (measurement) | Green-White 157B | White 155A (immature: Green-White 157A) |
| 54 | Bract variegation (observation) | Not variegated | Not variegated |
| 55 | Variegation pattern (observation) | NA | NA |
| 56 | Variegation color (measurement) | NA | NA |
| 57 | Pistil color (observation) | Yellow green 148C | Yellow green (Not coded) |
| 58 | Stigma color (observation) | Green (N138B) | Dark Green (Not Coded) |
| 59 | Peduncle thickness (measurement) | Medium | Medium |
| 60 | Peduncle length (measurement) | Average 69 mm | Long (mean of 68 mm) |
| 61 | Peduncle color (observation) | Green 143C | Yellow-Green 144B |
| 62 | Fruit shape (observation) | Globose | Globose |
| 63 | Fruit length (measurement) | About 28.7-29.3 mm | Medium (about 40 mm) |
| 64 | Fruit width (measurement) | About 28.7-29.3 mm | Medium (about 4.0 mm) |
| 65 | Fruit color (observation) | Green 134N, Fall; Red-Purple 60D-61A, when ripe in October | Unripe: Green 143B; Ripe: Orange-Red 33B to 43A. Highly variable depending on ripeness |
| 66 | Fragrance (observation) | None | Absent |
| 67 | Seed fertility (observation) | Not observed | High |
| 68 | Time to the first flowering (observation) | Medium (Mid-April-late May) | Medium (April-mid-May) |
| 69 | Blooming habit (observation) | Prolific | Many |
| 70 | Flowering season (observation) | One season | One season flowering |
| 71 | Flowering time (observation) | About 5-6 weeks | About 5-6 weeks |
| 72 | Deciduous or evergreen (observation) | Deciduous | Deciduous |
| 73 | Cold hardiness (observation) | To −20° C. | Medium (to −20° C.-no effect) |

TABLE 5-continued

Characteristics of 'Melissa's Mountain Snowfall' and Pam's Mountain Bouquet'
Color Descriptions are based upon the Royal Horticultural Society's (RHS) colour chart, 4th Edition 2001.

| | Character | 'Melissa's Mountain Snowfall' | 'Pam's Mountain Bouquet' |
|---|---|---|---|
| 74 | Heat tolerance (observation) | Strong (to 40° C.-no effect) | Strong (to 40° C.-no effect) |
| 75 | Pest resistance (observation) | No specific pests noted spots of brown anthracnose (Unidentified etiology - no control measures necessary) Brown N200A | Strong some leaf (no specific pests noted) |
| 76 | Disease resistance (observation) | Strong resistant to dogwood anthracnose and powdery mildew; some spot anthracnose especially on bracts | Strong resistant to dogwood anthracnose and powdery mildew; some spot anthracnose especially on bracts |
| 77 | Bark color | Exfoliating bark Greyed-Orange 177B and Green 143C; exfoliating areas Greyed-Brown 199C-199D | Greyed-Green 198B |
| 78 | Bark texture | Exfoliating | Smooth |
| 79 | Angle of emerging branches | 20°-35° from vertical stem | 20°-30° from vertical stem |
| 80 | Time to first leaf bud burst | Mid- to late-April | Mid- to late-April |
| 81 | Leaf Vein color (bottom side) | Yellow-Green 145B | Greyed-Green 192A |
| 82 | Immature Leaf color | Similar to fully expanded leaf color | Similar to fully expanded leaf color |
| 83 | Bract base | Truncate | Truncate |
| 84 | Bract margin | Entire | Entire |
| 85 | Vestiture | Puberulous, reticulate | Puberulous, reticulate |
| 86 | Flower/ inflorescence number | Mean = 31 | Mean = 34 |
| 87 | Seed shape | Flattened along length | Flattened along length |
| 88 | Seed color | Greyed Yellow 162D | Greyed Yellow 162D |
| 89 | Seed number | 0-17 per fruit | 0-17 per fruit |
| 90 | Bloom duration | 3-5 weeks (dried, dead bracts are retained as a "collar" on peduncle until fruit fall in Autumn) | 3-5 weeks (dried, dead bracts are retained as a " collar" on peduncle until fruit fall in Autumn) |

TABLE 5-continued

Characteristics of 'Melissa's Mountain Snowfall' and Pam's Mountain Bouquet'
Color Descriptions are based upon the Royal Horticultural Society's (RHS) colour chart, 4th Edition 2001.

| | Character | 'Melissa's Mountain Snowfall' | 'Pam's Mountain Bouquet' |
|---|---|---|---|
| 91 | Time of fruit ripening | Begins mid-August and Ripe in October | Begins mid- to late-August through October |
| 92 | Trunk diameter (at base) | Multiple stem variable. About 10-14 cm; numerous lenticels | 18 cm at 15 years of age |
| 93 | Anther color | Purple N79B | Greyed-purple N186A |
| 94 | Flower petal color | Yellow-green 145C | Yellow-green 145C |
| 95 | Style/Stigma description | Inconspicuous | Inconspicuous |

Botanical classification: *Cornus kousa* 'Melissa's Mountain Snowfall'.

Unique features: This tree features prolific flowering and exhibits fused bracts. About 80% of all bracts on the cultivar exhibit some degree of fusion (one side, two sides or three to four sides being fused), as shown in Table 6.

TABLE 6

Types of fused bracts observed on 'Melissa's Mountain Bouquet'

| Year | Not fused | Two sides fused | 3 sides fused | Fully Fused |
|---|---|---|---|---|
| 2016 (n = 101) | 29 (29%) | 23 (23%) | 17 (17%) | 32 (32%) |
| 2017 (n = 145) | 39 (27%) | 28 (19%) | 33 (23%) | 45 (31%) |
| 2019 (n = 123) | 7 (6%) | 12 (10%) | 14 (11%) | 90 (73%) |
| Mean | 25 (20.7%) | 21 (17.3%) | 21 (17.0%) | 55.7 (45.3%) |

Disease susceptibility: None noted. Powdery mildew caused by *Erysiphe pulchra* was not observed. There was some minor occurrence of spot anthracnose on bracts caused by *Elsinoe cornii* observed in 2017-2019. Most spots were discrete, less than 1 cm in diameter and various hues in the red-purple group N74C-D. Cold damage may also result in discoloration of bracts similar to spot anthracnose or over larger areas. Dogwood anthracnose caused by *Discula destructiva* has never been observed on 'Melissa's Mountain Snowfall'.

Insect damage: Minor insect damage on leaves.

REFERENCES

Wadl, P. A., M. T. Windham, R. E. Evans, and R. N. Trigiano. 2014. Three new cultivars of *Cornus kousa*: Empire, Pam's Mountain Bouquet, and Red Steeple. HortScience 49(9):1230-1233.

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Forward primer sequence
```

-continued

<400> SEQUENCE: 1 gcatttgtcc tttgtttgac at 22

<210> SEQ ID NO 2
<211> LENGTH: 22
<212> TYPE: DNA
<213> ORGANISM: Artificial Sequence
<220> FEATURE:
<223> OTHER INFORMATION: Reverse primer sequence

<400> SEQUENCE: 2 tttttcgcga agtgttctct ac 22

<210> SEQ ID NO 3
<211> LENGTH: 24
<212> TYPE: DNA
<213> ORGANISM: Artificial Sequence
<220> FEATURE:
<223> OTHER INFORMATION: Forward primer sequence

<400> SEQUENCE: 3 gtcaaatttt tgatctttct ctct 24

<210> SEQ ID NO 4
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 4 ggagagacag agtacagtag aggt 24

<210> SEQ ID NO 5
<211> LENGTH: 24
<212> TYPE: DNA
<213> ORGANISM: Artificial Sequence
<220> FEATURE:
<223> OTHER INFORMATION: Forward primer sequence

<400> SEQUENCE: 5 aatttaggtt aaggttttga tttg 24

<210> SEQ ID NO 6
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 6 agagagaata ggttacagca tcat 24

<210> SEQ ID NO 7
<211> LENGTH: 22
<212> TYPE: DNA
<213> ORGANISM: Artificial Sequence
<220> FEATURE:
<223> OTHER INFORMATION: Forward primer sequence

<400> SEQUENCE: 7 tgtcactgct tacagaaaca at 22

-continued

<210> SEQ ID NO 8
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 8 tatgacgaga ttgtataagt tgct 24

<210> SEQ ID NO 9
<211> LENGTH: 23
<212> TYPE: DNA
<213> ORGANISM: Artificial Sequence
<220> FEATURE:
<223> OTHER INFORMATION: Forward primer sequence

<400> SEQUENCE: 9 ccaagtcagt ttggtagtaa ttc 23

<210> SEQ ID NO 10
<211> LENGTH: 23
<212> TYPE: DNA
<213> ORGANISM: Artificial Sequence
<220> FEATURE:
<223> OTHER INFORMATION: Reverse primer sequence

<400> SEQUENCE: 10 agtgcaactt ttacttgcta tgt 23

<210> SEQ ID NO 11
<211> LENGTH: 24
<212> TYPE: DNA
<213> ORGANISM: Artificial Sequence
<220> FEATURE:
<223> OTHER INFORMATION: Forward primer sequence

<400> SEQUENCE: 11 cttaagtcac aaagacaatg aaat 24

<210> SEQ ID NO 12
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 12 aagagagttc agatttatct ttgc 24

<210> SEQ ID NO 13
<211> LENGTH: 20
<212> TYPE: DNA
<213> ORGANISM: Artificial Sequence
<220> FEATURE:
<223> OTHER INFORMATION: Forward primer sequence

<400> SEQUENCE: 13 agcactcata gtccttgcac 20

<210> SEQ ID NO 14
<211> LENGTH: 24
<212> TYPE: DNA
<213> ORGANISM: Artificial Sequence
<220> FEATURE:
<223> OTHER INFORMATION: Reverse primer sequence -continued

```
<400> SEQUENCE: 14

gttaaaacga agaagataca acaa                                          24


<210> SEQ ID NO 15
<211> LENGTH: 24
<212> TYPE: DNA
<213> ORGANISM: Artificial Sequence
<220> FEATURE:
<223> OTHER INFORMATION: Forward primer sequence

<400> SEQUENCE: 15

gaaagagata aaagatggtt caat                                          24


<210> SEQ ID NO 16
<211> LENGTH: 22
<212> TYPE: DNA
<213> ORGANISM: Artificial Sequence
<220> FEATURE:
<223> OTHER INFORMATION: Reverse primer sequence

<400> SEQUENCE: 16

cttatagagt aagcccacca tc                                            22
```

The invention claimed is:

1. A new and distinct cultivar of Dogwood tree, *Cornus kousa*, named 'Melissa's MOUNTAIN Snowfall', as illustrated and described.

* * * * *